US012653495B2

(12) United States Patent  (10) Patent No.: US 12,653,495 B2
Kusu  (45) Date of Patent: Jun. 16, 2026

(54) MEDICAL IMAGING APPARATUS, METHOD, AND STORAGE MEDIUM

(71) Applicant: TERUMO KABUSHIKI KAISHA, Tokyo (JP)

(72) Inventor: Kohtaroh Kusu, Ebina Kanagawa (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 0 days.

(21) Appl. No.: 18/898,587

(22) Filed: Sep. 26, 2024

(65) Prior Publication Data

US 2025/0017560 A1      Jan. 16, 2025

Related U.S. Application Data

(63) Continuation of application No. PCT/JP2023/008440, filed on Mar. 7, 2023.

(30) Foreign Application Priority Data

Mar. 29, 2022    (JP) ................................. 2022-054470

(51) Int. Cl.
*A61B 8/00* (2006.01)
*A61B 8/08* (2006.01)
(Continued)

(52) U.S. Cl.
CPC .............. *A61B 8/0891* (2013.01); *A61B 8/12* (2013.01); *A61B 8/5223* (2013.01);
(Continued)

(58) Field of Classification Search
CPC .................................................. A61B 8/0891
See application file for complete search history.

(56) References Cited

U.S. PATENT DOCUMENTS

2015/0073279 A1    3/2015  Cai et al.
2019/0021694 A1    1/2019  Sakaguchi
(Continued)

FOREIGN PATENT DOCUMENTS

JP          H07-59777 A      3/1995
JP          2016-530043 A    9/2016
(Continued)

OTHER PUBLICATIONS

Extended European Search Report mailed Mar. 18, 2025 in corresponding European Patent Application No. 23779289.0, 37 pages.
(Continued)

*Primary Examiner* — Joseph M Santos Rodriguez
(74) *Attorney, Agent, or Firm* — Kim & Stewart LLP

(57) ABSTRACT

A medical imaging apparatus for generating a three-dimensional image of a vessel includes a catheter including a probe and insertable into the vessel, the catheter being configured to generate cross-sectional images of the vessel from ultrasonic signals emitted from the probe and received by the probe, and a processor configured to: control the catheter to emit the signals and acquire a series of cross-sectional images of the vessel therefrom, calculate a series of feature values of the vessel corresponding to the series of cross-sectional images, determine local maximums of variations in the series of feature values, select two or more of the cross-sectional images corresponding to the local maximums, and generate a three-dimensional image of the vessel using the selected images.

20 Claims, 16 Drawing Sheets

(51) Int. Cl.

| | |
|---|---|
| *A61B 8/12* | (2006.01) |
| *G06T 7/00* | (2017.01) |
| *G06T 7/62* | (2017.01) |

(52) U.S. Cl.
CPC .............. *G06T 7/0012* (2013.01); *G06T 7/62* (2017.01); *G06T 2207/10132* (2013.01); *G06T 2207/20081* (2013.01); *G06T 2207/20084* (2013.01); *G06T 2207/30101* (2013.01)

(56) References Cited

U.S. PATENT DOCUMENTS

| | | | |
|---|---|---|---|
| 2019/0282182 A1 | 9/2019 | Scott et al. | |
| 2020/0294659 A1 | 9/2020 | Gopinath et al. | |

FOREIGN PATENT DOCUMENTS

| | | |
|---|---|---|
| JP | 2021-517034 A | 7/2021 |
| WO | 2017/164071 A1 | 9/2017 |

OTHER PUBLICATIONS

Sihan, Kenji et al., "Retrospective Image-Based Gating of Intracoronary Optical Coherence Tomography: Implications for Quantitative Analysis", EuroIntervention, vol. 6, No. 9, p. 1098-1103, (2011).

Zheng, Sun et al., "Suppression of Cardiac Motion Artifacts in Sequential Intracoronary Optical Coherence Images", Journal of Medical Imaging and Health Informatics, vol. 6, No. 7, p. 1787-1793, (2016).

Nadkarni, Seemantini K. et al., "Image-Based Cardiac Gating for Three-Dimensional Intravascular Ultrasound Imaging", Ultrasound in Medicine & Biology, vol. 31, No. 1, p. 53-63, (2005).

European Office Action dated Jan. 19, 2026 in corresponding European Patent Application No. 23779289.0, 9 pages.

Chatzizisis Yiannis S et al: "Clinical validation of an algorithm for rapid and accurate automated segmentation of intracoronary optical coherence tomography images", International Journal of Cardiology, Elsevier, Amsterdam, NL, vol. 172, No. 3, Jan. 24, 2014 (Jan. 24, 2014), pp. 568-580.

Bargsten Lennart et al: "Capsule networks for segmentation of small intravascular ultrasound image datasets", International Journal of Computer Assisted Radiology and Surgery, Springer, DE, vol. 16, No. 8, Jun. 14, 2021 (Jun. 14, 2021), pp. 1243-1254.

Yang Ji et al: "IVUS-Net: An Intravascular Ultrasound Segmentation Network", Dec. 8, 2018 (Dec. 8, 2018), Advances in Databases and Information Systems; [Lecture Notes in Computer Science; Lect. Notes Computer], Springer International Publishing, CHAM, pp. 367-377.

SEGMENTATION DATA Sm

O (x, y)

BOUNDARY OF
BLOOD VESSEL y x

FEATURE VALUE
= COORDINATES (x, y) OF CENTROID O OF BLOOD VESSEL

SEGMENTATION DATA Sm

D1

D2

O

BOUNDARY OF
BLOOD VESSEL

FEATURE VALUE = MEAN LUMEN DIAMETER D OF BLOOD VESSEL $$\text{MEAN LUMEN DIAMETER D} = \frac{\text{MAXIMUM DIAMETER D1} + \text{MINIMUM DIAMETER D2}}{2}$$

B

IDENTIFY
NECESSARY FRAME

A

COMPARATIVE EXAMPLE

PRESENT EMBODIMENT

FIG. 16

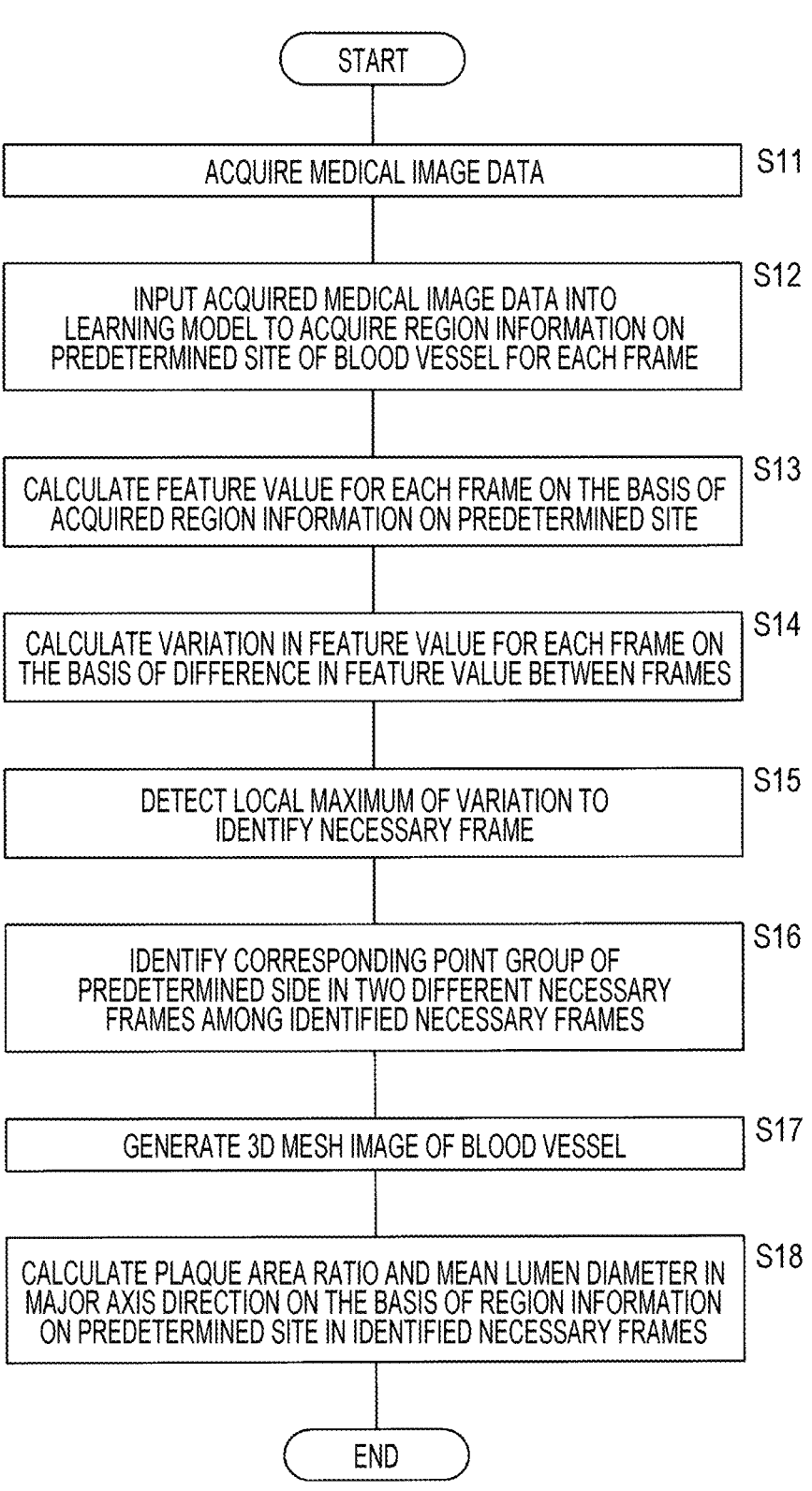

START

ACQUIRE MEDICAL IMAGE DATA — S11

INPUT ACQUIRED MEDICAL IMAGE DATA INTO
LEARNING MODEL TO ACQUIRE REGION INFORMATION ON
PREDETERMINED SITE OF BLOOD VESSEL FOR EACH FRAME — S12

CALCULATE FEATURE VALUE FOR EACH FRAME ON THE BASIS OF
ACQUIRED REGION INFORMATION ON PREDETERMINED SITE — S13

CALCULATE VARIATION IN FEATURE VALUE FOR EACH FRAME ON
THE BASIS OF DIFFERENCE IN FEATURE VALUE BETWEEN FRAMES — S14

DETECT LOCAL MAXIMUM OF VARIATION TO
IDENTIFY NECESSARY FRAME — S15

IDENTIFY CORRESPONDING POINT GROUP OF
PREDETERMINED SIDE IN TWO DIFFERENT NECESSARY
FRAMES AMONG IDENTIFIED NECESSARY FRAMES — S16

GENERATE 3D MESH IMAGE OF BLOOD VESSEL — S17

CALCULATE PLAQUE AREA RATIO AND MEAN LUMEN DIAMETER IN
MAJOR AXIS DIRECTION ON THE BASIS OF REGION INFORMATION
ON PREDETERMINED SITE IN IDENTIFIED NECESSARY FRAMES — S18

END

MEDICAL IMAGING APPARATUS, METHOD, AND STORAGE MEDIUM

CROSS-REFERENCE TO RELATED APPLICATION

This application is a continuation of International Patent Application No. PCT/JP2023/008440 filed Mar. 7, 2023, which is based upon and claims the benefit of priority from Japanese Patent Application No. 2022-054470, filed Mar. 29, 2022, the entire contents of which are incorporated herein by reference.

BACKGROUND

Technical Field

Embodiments described herein relate generally to a medical imaging apparatus, a method, and a storage medium.

Related Art

There is a conventional image diagnosis apparatus that generates a blood vessel cross-sectional image on the basis of an ultrasound signal emitted to a vascular tissue and received by an imaging core accommodated in a catheter inserted into a blood vessel.

When acquiring a medical image such as an intravascular ultrasound (IVUS) image, there is a possibility that the catheter moves back and forth and left and right relative to a coronary artery due to the influence of heartbeat. For this reason, blood vessel cross-sectional images that are acquired while pulling back the catheter at a constant speed may not be accurately reproduced. It is conceivable to suppress the influence of heartbeat by simultaneously acquiring electrocardiogram information together with the medical image and extracting only frames at specific intervals on the basis of the acquired electrocardiogram information.

The electrocardiogram information, however, is not always obtained under percutaneous coronary intervention (PCI), and so the three-dimensional shape of the blood vessel may not be reproduced accurately.

SUMMARY

Embodiments of the present disclosure provide a medical imaging apparatus, a method, and a storage medium for generating a fine three-dimensional image (3D image) of a blood vessel by extracting a limited number of cross-sectional images at specific intervals.

In one embodiment, a medical imaging apparatus for generating a three-dimensional image of a vessel, comprises: a catheter including a probe and insertable into the vessel, wherein the catheter is configured to generate cross-sectional images of the vessel from ultrasonic signals emitted from the probe and received by the probe; and a processor configured to: control the catheter to emit the signals and acquire a series of cross-sectional images of the vessel therefrom, calculate a series of feature values of the vessel corresponding to the series of cross-sectional images, determine local maximums of variations in the series of feature values, select two or more of the cross-sectional images corresponding to the local maximums, and generate a three-dimensional image of the vessel using the selected images.

According to such an embodiment, it is possible to generate a fine 3D image of a blood vessel by extracting a limited number of cross-sectional images at specific intervals.

BRIEF DESCRIPTION OF THE DRAWINGS

FIG. 16 is a diagram illustrating an example of a process performed by the information processing apparatus.

DETAILED DESCRIPTION

Figure 1:
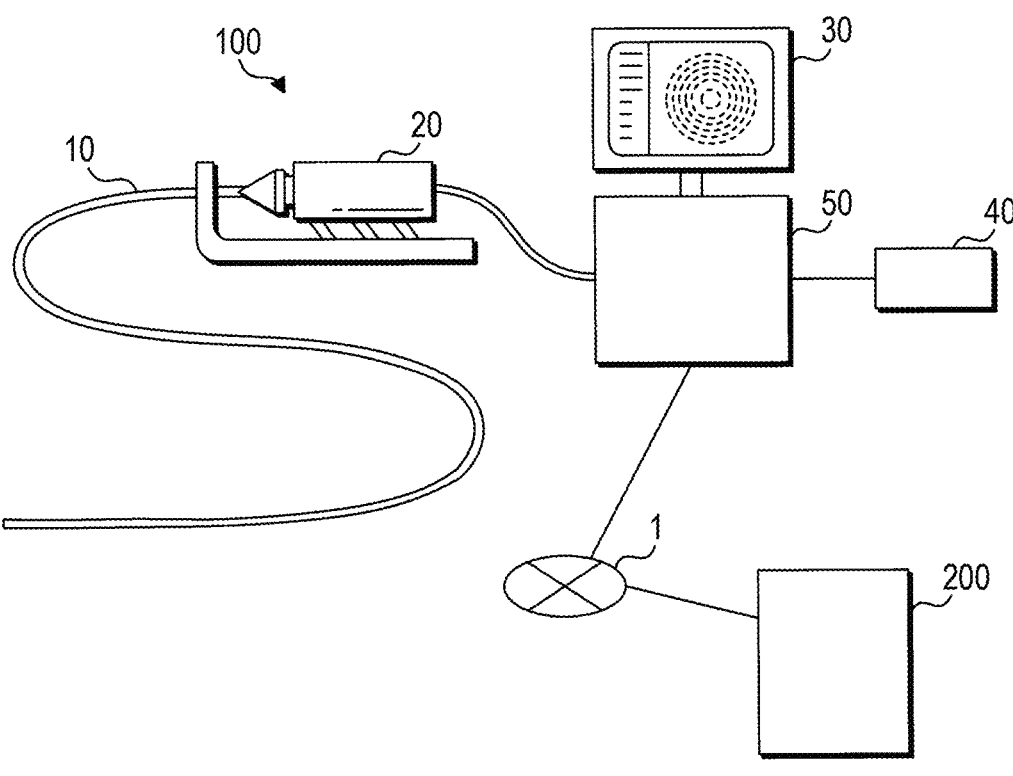
FIG. 1 is a diagram illustrating a configuration of an information processing system according to an embodiment.

Hereinafter, embodiments of the present disclosure will be described with reference to the drawings. FIG. 1 is a diagram illustrating a configuration of an information processing system 100 according to one embodiment. The information processing system 100 is, for example, a medical imaging system or apparatus or a diagnostic imaging system or apparatus for performing intravascular imaging or image diagnosis used for cardiac catheter treatment or PCI. The cardiac catheter treatment is a method of treating a narrowed portion of a coronary artery by inserting a catheter from a blood vessel such as a base of a leg, an arm, or a wrist. For intravascular imaging, there are two methods: an IVUS method; and an optical coherence tomography method, e.g., optical frequency domain imaging (OFDI) and optical coherence tomography (OCT). The IVUS uses reflection of ultrasound to interpret the inside of a blood vessel in a tomographic image. Specifically, a thin catheter equipped with an ultra-small sensor at its distal end is inserted into the coronary artery, and after passing to a lesion, a medical image representing the inside of a blood vessel can be generated using ultrasound transmitted from the sensor. The OFDI uses near-infrared rays to interpret a state of a blood vessel with a high-resolution image. Specifically, as in the IVUS, a catheter is inserted into a blood vessel, near-infrared rays are emitted from its distal end, a cross-section of the blood vessel is measured by interferometry, and a medical image is generated. Furthermore, the OCT is intravascular image diagnosis to which near-infrared rays and optical fiber technology are applied. A blood vessel will be described herein as an example of a luminal organ. Furthermore, the medical image or medical image data includes one generated by the IVUS, the OFDI, or the OCT, but the case of using the IVUS method will be mainly described herein below.

The information processing system 100 includes a catheter 10, a motor drive unit (MDU) 20, a display apparatus 30, an input apparatus 40, and an information processing apparatus 50. A server 200 is connected to the information processing apparatus 50 via a communication network 1.

The catheter 10 is an image diagnosis catheter for obtaining an ultrasound tomographic image of a blood vessel by the IVUS method. The catheter 10 has an ultrasound probe provided at its distal end for obtaining an ultrasound tomographic image of a blood vessel. The ultrasound probe includes an ultrasound transducer that emits ultrasound in a blood vessel, and an ultrasound sensor that receives a reflected wave (i.e., an ultrasound echo) reflected by a structure such as a biological tissue of the blood vessel or a medical device. The ultrasound probe is configured to be movable back and forth along a longitudinal direction of the blood vessel while rotating in a circumferential direction of the blood vessel.

The MDU 20 is a drive apparatus to which the catheter 10 can be detachably attached, and drives a built-in motor in response to the operation made by a medical worker to control the motion of the catheter 10 inserted into a blood vessel. The MDU 20 can rotate the ultrasound probe of the catheter 10 in the circumferential direction while moving the ultrasound probe from the distal side to the proximal side (i.e., pull-back operation). The ultrasound probe continuously scans the inside of the blood vessel at predetermined time intervals, and outputs reflected wave data of the detected ultrasound to the information processing apparatus 50.

The information processing apparatus 50 is a medical imaging apparatus that acquires medical image data representing time-series (i.e., a plurality of frames of) cross-sectional images of the blood vessel on the basis of the reflected wave data output from the ultrasound probe of the catheter 10. Since the ultrasound probe scans the inside of the blood vessel while moving from the distal side to the proximal side in the blood vessel, a plurality of medical images in chronological order is tomographic images of the blood vessel observed at a plurality of points from the distal side to the proximal side.

The display apparatus 30 includes a liquid crystal display panel (LCD), an organic EL display (OLED) panel, or the like, and can display a result of processing executed by the information processing apparatus 50. Furthermore, the display apparatus 30 can display the medical image generated or acquired by the information processing apparatus 50.

The input apparatus 40 is an input interface such as a keyboard and a mouse that receives input of various setting values, an operation for the information processing apparatus 50, and the like when an examination is made. The input apparatus 40 may be a touch panel, a software key, a hardware key, or the like provided in the display apparatus 30.

The server 200 is, for example, a data server, and may include an image database (DB) in which the medical image data is accumulated.

Figure 2:
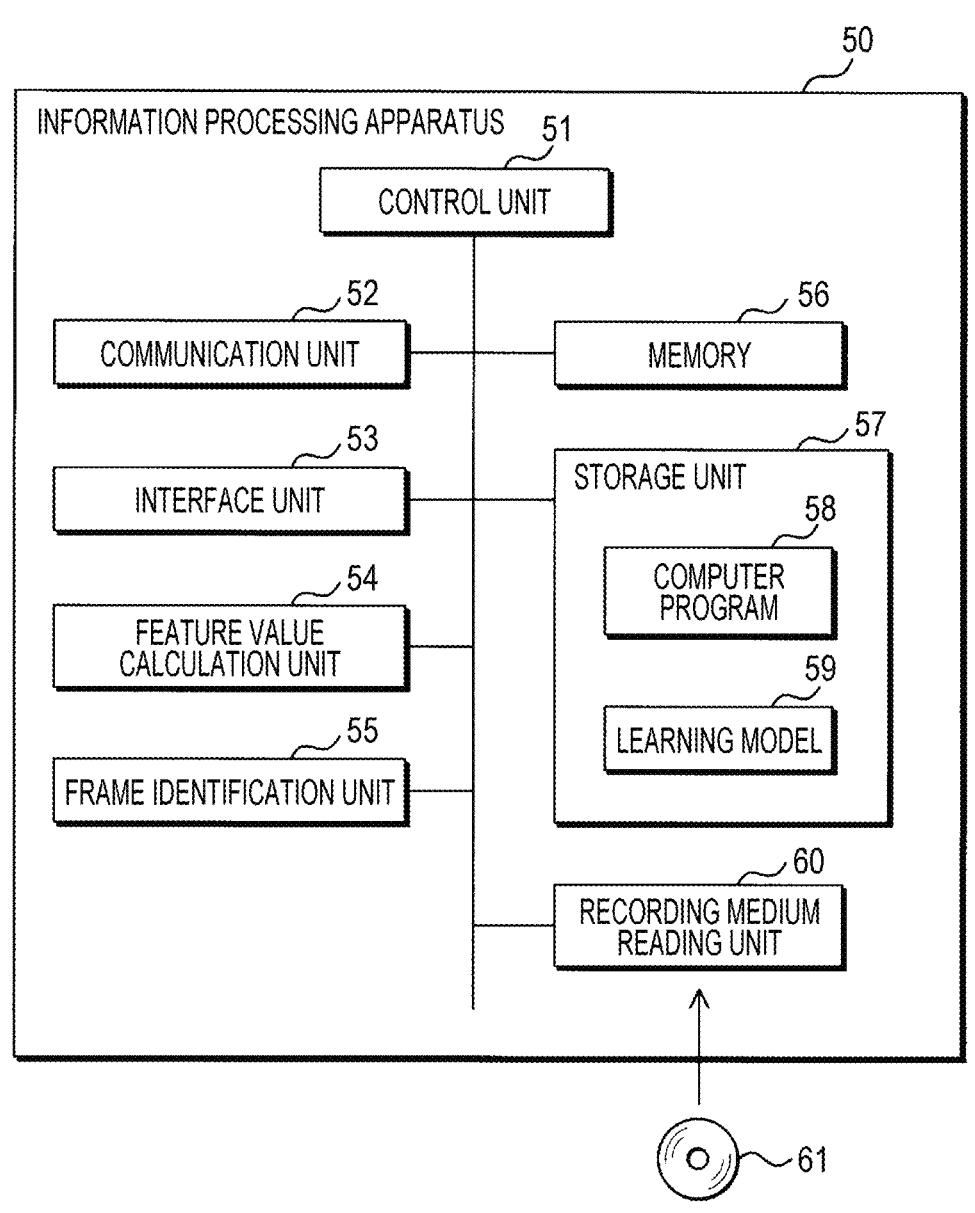
FIG. 2 is a diagram illustrating a configuration of an information processing apparatus of the information processing system.

FIG. 2 is a diagram illustrating an example of a configuration of the information processing apparatus 50. The information processing apparatus 50 includes a control unit 51 that controls the entire information processing apparatus 50, a communication unit 52, an interface unit 53, a feature value calculation unit 54, a frame identification unit 55, a memory 56, a storage unit 57, and a recording medium reading unit 60. The storage unit 57 stores a computer program 58 and a learning model 59.

The feature value calculation unit 54 and the frame identification unit 55 may be implemented by hardware (e.g., circuits), may be implemented by software (e.g., the computer program 58), or may be implemented by both hardware and software. The information processing apparatus 50 may include a plurality of distributed information processing apparatuses to perform its function.

For example, the control unit 51 is a control circuit that includes one or more processors such as a predetermined number of central processing units (CPUs), micro-processing units (MPUs), graphics processing units (GPUs), general-purpose computing on graphics processing units (GPGPUs), or tensor processing units (TPUs). Furthermore, the control unit 51 may include a combination of digital signal processors (DSPs), field-programmable gate arrays (FPGAs), quantum processors, and the like.

The control unit 51 can execute processing according to the computer program 58. That is, the processing executed by the control unit 51 corresponds to processing executed in accordance with the computer program 58.

The memory 56 may include a semiconductor memory, such as a static random access memory (SRAM), a dynamic random access memory (DRAM), or a flash memory. Loading the computer program 58 into the memory 56 enables the control unit 51 to execute the computer program 58.

The communication unit 52 includes, for example, a communication module or a network interface circuit and has a capability of communicating with the server 200 over the communication network 1. Furthermore, the communication unit 52 may have a capability of communicating with an external device (not illustrated) connected to the communication network 1. The communication unit 52 may acquire, from the server 200, medical image data representing a plurality of frames of cross-sectional images of a blood vessel.

The interface unit 53 provides an interface function between the catheter 10, the display apparatus 30, and the input apparatus 40. The information processing apparatus 50 can transmit and receive data or information to and from the catheter 10, the display apparatus 30, and the input apparatus 40 via the interface unit 53. The interface unit 53 may acquire, from the catheter 10, medical image data representing a plurality of frames of cross-sectional images of a blood vessel.

The recording medium reading unit 60 can include, for example, an optical disc drive, and the computer program 58 recorded on a recording medium 61 (for example, an optically readable disc storage medium such as a CD-ROM) can be read by the recording medium reading unit 60 and stored into the storage unit 57. The computer program 58 is loaded onto the memory 56 and executed by the control unit 51. Note that the computer program 58 may be downloaded from an external device via the communication unit 52 and stored into the storage unit 57.

The storage unit 57 can include, for example, a hard disk, a semiconductor memory, or the like, and can store necessary information (for example, data being processed by the information processing apparatus 50, a processing result, and the like). The feature value calculation unit 54 functions as a calculation unit, and calculates a feature value of a blood vessel for each frame on the basis of the medical image data acquired via the interface unit 53 or the communication unit 52. Details of the feature value will be described later.

The frame identification unit 55 functions as a detection unit and an identification unit, detects a local maximum (i.e., a peak) of variations in the feature value between frames, and identifies a plurality of necessary frames from among the plurality of frames on the basis of the detected local maximum. Details of the method of identifying a necessary frame will be described later.

Figure 3:
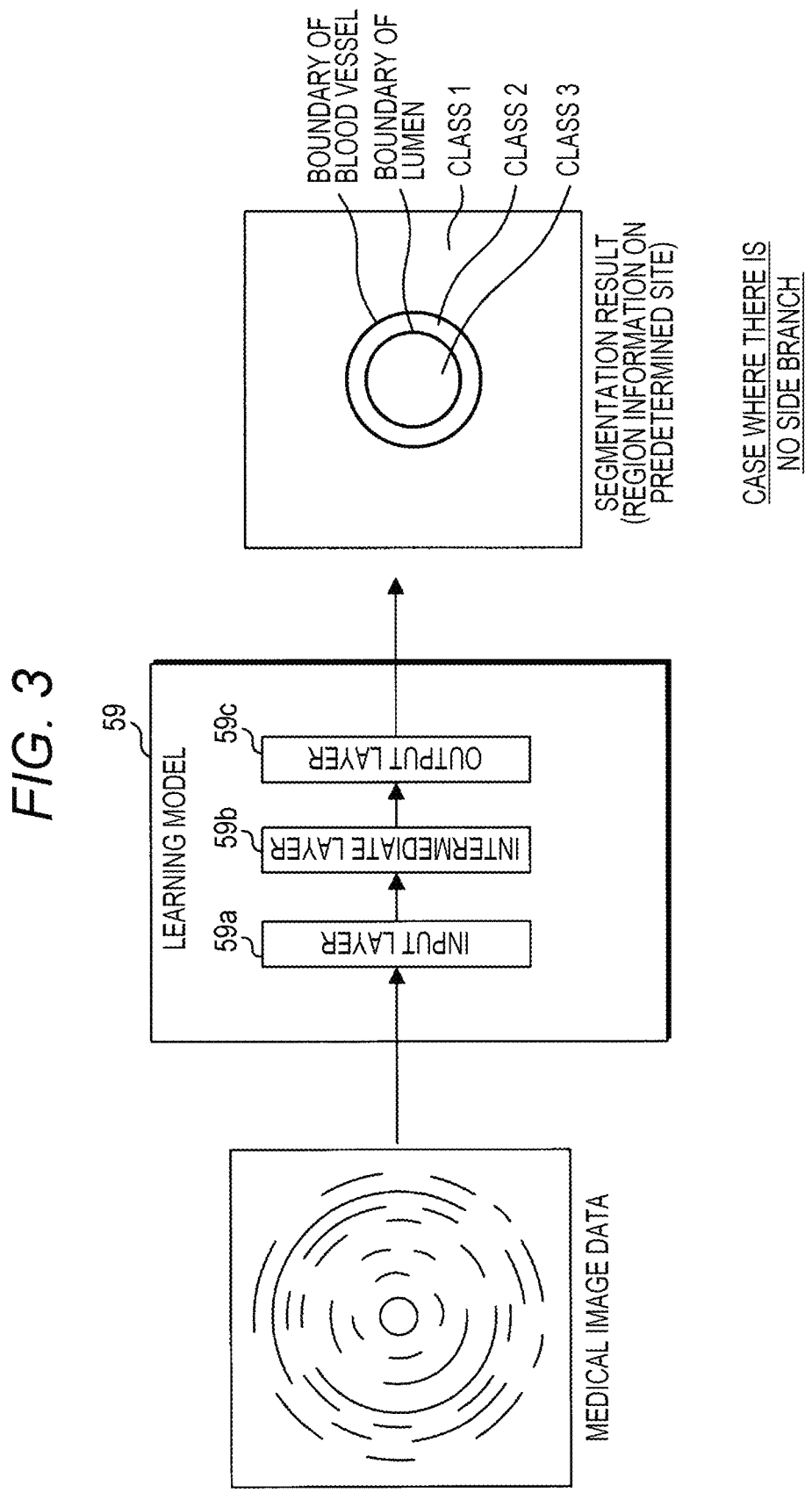
FIG. 3 is a diagram illustrating a first example of processing using a learning model.

FIG. 3 is a diagram illustrating a first example of processing using the learning model 59. In the first example, it is assumed that the blood vessel has no side branch. The learning model 59 includes an input layer 59a, an intermediate layer 59b, and an output layer 59c, and can be created as a U-Net, for example. The intermediate layer 59b includes a plurality of encoders and a plurality of decoders. The plurality of encoders repeat convolution processing on the medical image data input into the input layer 59a. The plurality of decoders repeat upsampling (i.e., deconvolution) processing on the image convolved by the encoders. When decoding the convolved image, processing of adding a feature map generated by the encoders to the image to be subjected to the deconvolution processing is executed. As a result, position information lost by the convolution processing can be retained, and more accurate segmentation to which class each pixel belongs can be output.

When the medical image data is input, the learning model 59 can output segmentation data (i.e., region information on a predetermined site). The segmentation data is obtained by classifying each pixel of the medical image data into a class. The learning model 59 can classify pixels of each piece of the input medical image data into, for example, three classes: classes 1, 2, and 3. Class 1 indicates "Background" that is a region outside the blood vessel. Class 2 indicates "Plaque+Media", that is a region of the blood vessel containing the plaque. Class 3 indicates "Lumen" that is the lumen of the blood vessel. Therefore, a boundary between pixels classified into Class 2 and pixels classified into Class 3 indicates a boundary of the lumen, and a boundary between pixels classified into Class 1 and pixels classified into Class 2 indicates a boundary of the blood vessel. That is, when the medical image data is input, the learning model 59 can output region information on a predetermined site of the blood vessel (that is, information indicating the boundary of the lumen and the boundary of the blood vessel). The predetermined site includes the boundary of the blood vessel and the boundary of the lumen. The region information is coordinate data of pixels indicating both the boundary of the lumen and the boundary of the blood vessel. Note that the learning model 59 is not limited to the U-Net, and may be, for example, a generative adversarial network (GAN), Seg-Net, or the like.

A method of generating the learning model 59 can be as follows. First, first training data including medical image data representing a cross-sectional image of a blood vessel and segmentation data indicating a class of each pixel of the medical image data is acquired. For example, the first training data may be collected and stored in the server 200 and acquired from the server 200. Next, the learning model 59 may be generated on the basis of the first training data to output segmentation data when the medical image data representing the cross-sectional image of a blood vessel is input into the learning model 59. In other words, the learning model 59 may be generated on the basis of the first training data to output region information on each of the boundary of a lumen and the boundary of a blood vessel when the medical image data representing the cross-sectional image of the blood vessel is input into the learning model 59.

Figure 4:
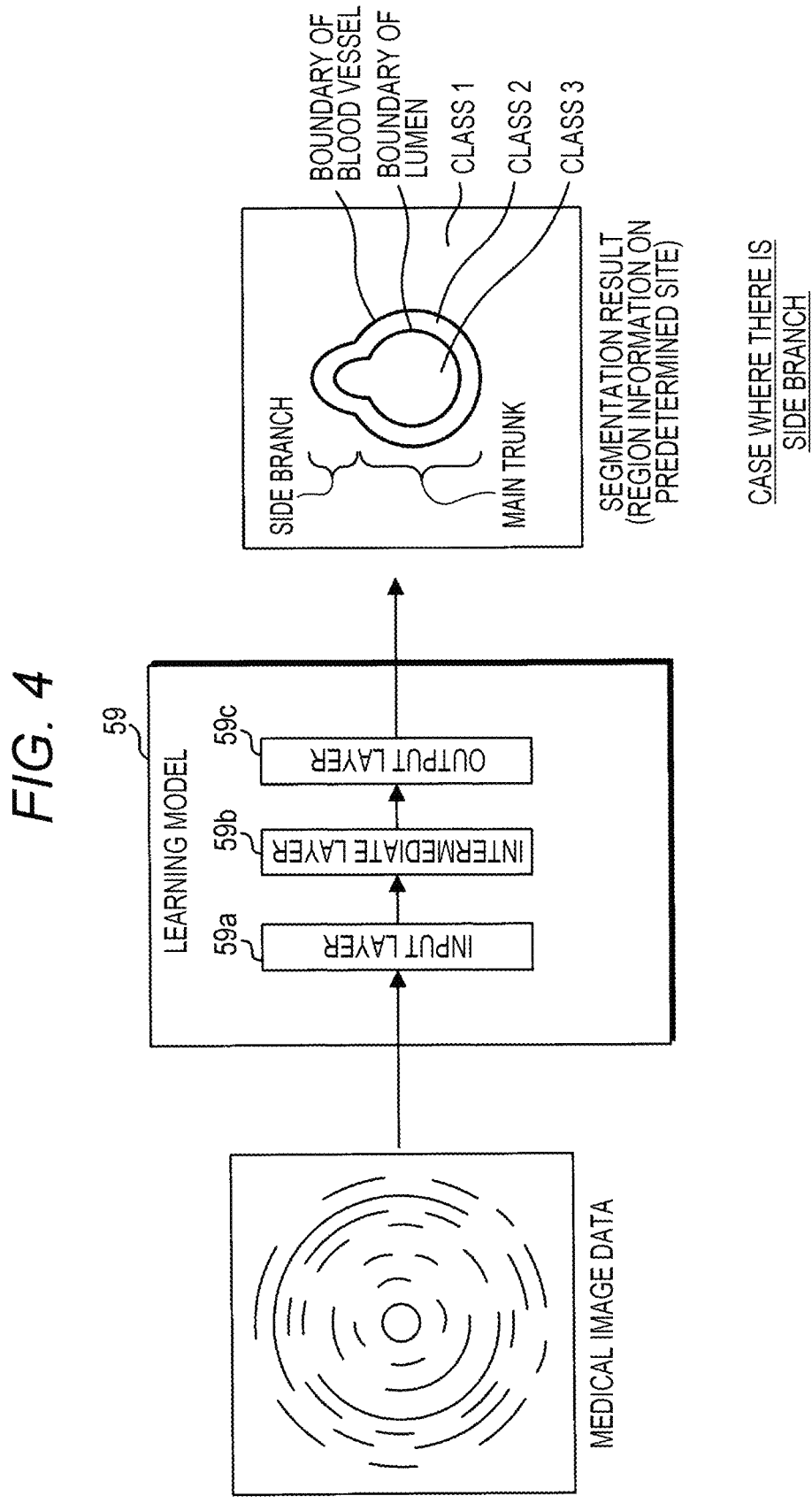
FIG. 4 is a diagram illustrating a second example of the processing using the learning model.

FIG. 4 is a diagram illustrating a second example of the processing using the learning model 59. In the second example, it is assumed that the blood vessel has a side branch. As in the first example, when the medical image data is input into the learning model 59, the learning model 59 outputs region information on each of the boundary of the lumen and the boundary of the blood vessel. The learning model 59 can output region information on the boundary of the lumen and the boundary of the blood vessel of each of the main trunk of the blood vessel and the side branch connected to the main trunk. Other configurations are similar to those of the first example, and thus the description thereof will be omitted.

Figure 5:
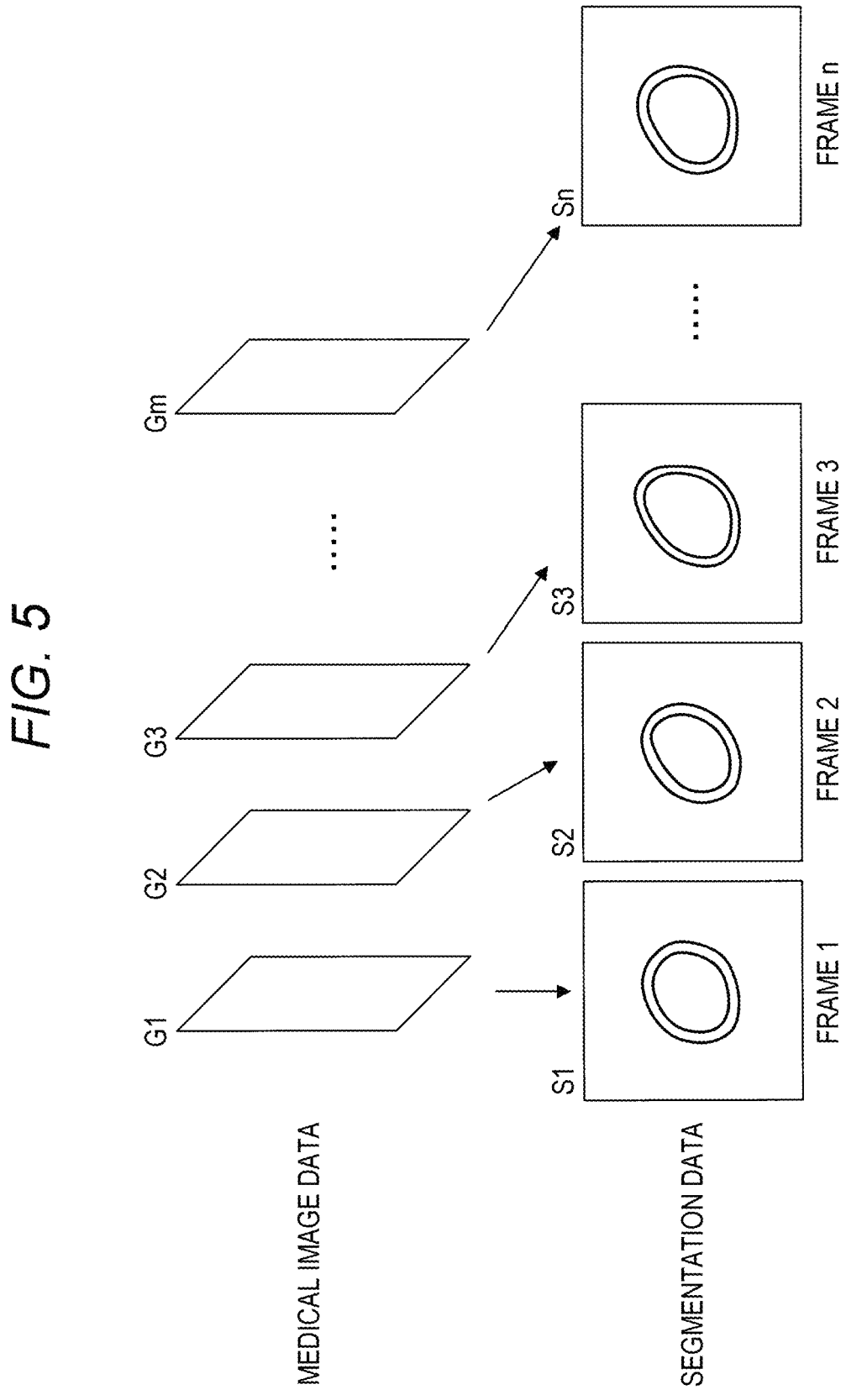
FIG. 5 is a diagram illustrating an example of segmentation data output by the learning model.

FIG. 5 is a diagram illustrating an example of segmentation data output by the learning model 59. Medical image data (G1, G2, G3, . . . , Gn) including a plurality of frames (frames 1 to n) of cross-sectional images is acquired from a plurality of time-series cross-sectional images of the blood vessel obtained as a result of one pull-back operation. The acquired medical image data is data to be input into the learning model 59. The learning model 59 outputs segmentation data (S1, S2, S3, . . . , Sn) corresponding to frames 1 to n on a one-to-one basis. As described with reference to FIG. 3 or 4, each piece of segmentation data includes the region information on the boundary of the blood vessel and the boundary of the lumen.

In a case where medical image data representing a plurality of frames of cross-sectional images of a blood vessel is input, the control unit 51 inputs the acquired medical image data to the learning model 59 that outputs region information on a predetermined site of a blood vessel to acquire region information on the predetermined site of the blood vessel for each frame. The control unit 51 or the feature value calculation unit 54 can calculate the feature value of the blood vessel for each frame on the basis of the acquired region information.

Next, the feature value calculated by the feature value calculation unit 54 will be described. As with electrocardiogram information and the like, the feature value may be a physical quantity on the basis of which specific heartbeat intervals synchronized with heartbeat can be identified, and may be, for example, a physical quantity that can express a relative positional relationship between the catheter and the blood vessel that changes with heartbeat. Herein, as examples of the feature value, the centroid of the blood vessel and the mean lumen diameter will be described, but the feature value is not limited to such examples. Note that the lumen varies in a manner that depends on the plaque area ratio (i.e., the plaque burden), so that the blood vessel is more preferable.

Figure 6A:
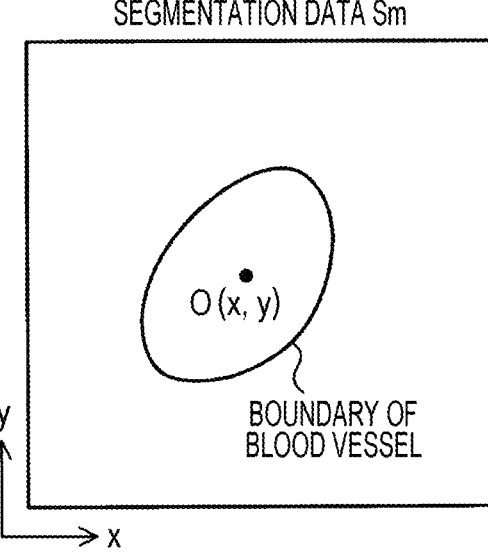
FIG. 6A is a diagram illustrating an example of a feature value.
Figure 6B:
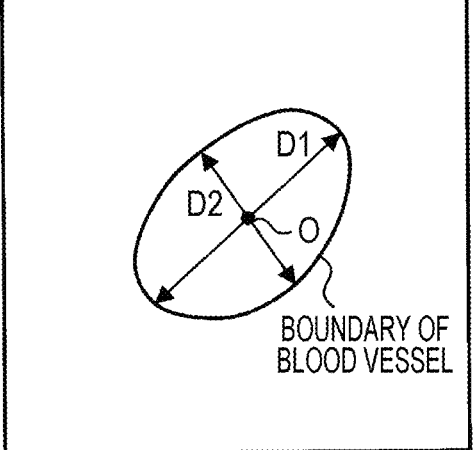
FIG. 6B is a diagram illustrating an example of the feature value.

FIGS. 6A and 6B are diagrams illustrating examples of the feature value. The feature value can be calculated for each piece of segmentation data S1, S2, S3, . . . , and Sn corresponding to the frames 1 to n on a one-to-one basis illustrated in FIG. 5. In the example in FIGS. 6A and 6B, the segmentation data Sm corresponding to the frame m will be described. Here, m can be 1 to n.

FIG. 6A illustrates a case where coordinates (x, y) of a centroid O of the blood vessel are used as the feature value. Specifically, the centroid O of the blood vessel is a centroid position of a shape defined by the boundary of the blood vessel represented by the segmentation data. The centroid O(x, y) can be calculated as follows. In xy two-dimensional coordinates, coordinates of a plurality of mass points (all masses are assumed to be 1) constituting the blood vessel are denoted as (x1, y1), (x2, y2), . . . , and (xn, yn). Here, n denotes the number of mass points. On the basis of moment equilibrium around the centroid O in the x-axis direction, an x coordinate of the centroid O can be obtained by x=(x1+ x2+ . . . +xn)/n. Furthermore, on the basis of moment equilibrium around the centroid O in the y-axis direction, a y coordinate of the centroid O can be obtained by y=(y1+ y2+ . . . +yn)/n. Furthermore, the centroid O(x, y) may be obtained, for example, as a center position of a circle approximate to the boundary of the blood vessel. Furthermore, the centroid O(x, y) may be obtained, for example, by setting a plurality of vertices on the boundary of the blood vessel and obtaining the centroid of a polygon including the vertices.

FIG. 6B illustrates a case where a mean lumen diameter D of the blood vessel is used as the feature value. Specifically, the mean lumen diameter D may be calculated as follows: a maximum diameter D1 and a minimum diameter D2 of line segments passing through the centroid O of the blood vessel are obtained, and the mean of the maximum diameter D1 and the minimum diameter D2 is obtained as the mean lumen diameter D. Hereinafter, the centroid position of the blood vessel is used as the feature value, but the mean lumen diameter D may be used.

As described above, the feature value calculation unit 54 can calculate the centroid position O(x, y) of the blood vessel for each of the plurality of frames.

The feature value calculation unit 54 calculates variations in the feature value for each of the plurality of frames. For example, the centroid position for the frame (i−1) is denoted as {x(i−1), y(i−1)}, and the centroid position for the frame i is denoted as {xi, yi}. A variation Δi in feature value for the frame i is a variation from the centroid position {x(i−1), y(i−1)} to the centroid position {xi, yi}, and can be expressed by a distance between the two centroid positions {x(i−1), y(i−1)} and {xi, yi}.

Figure 7:
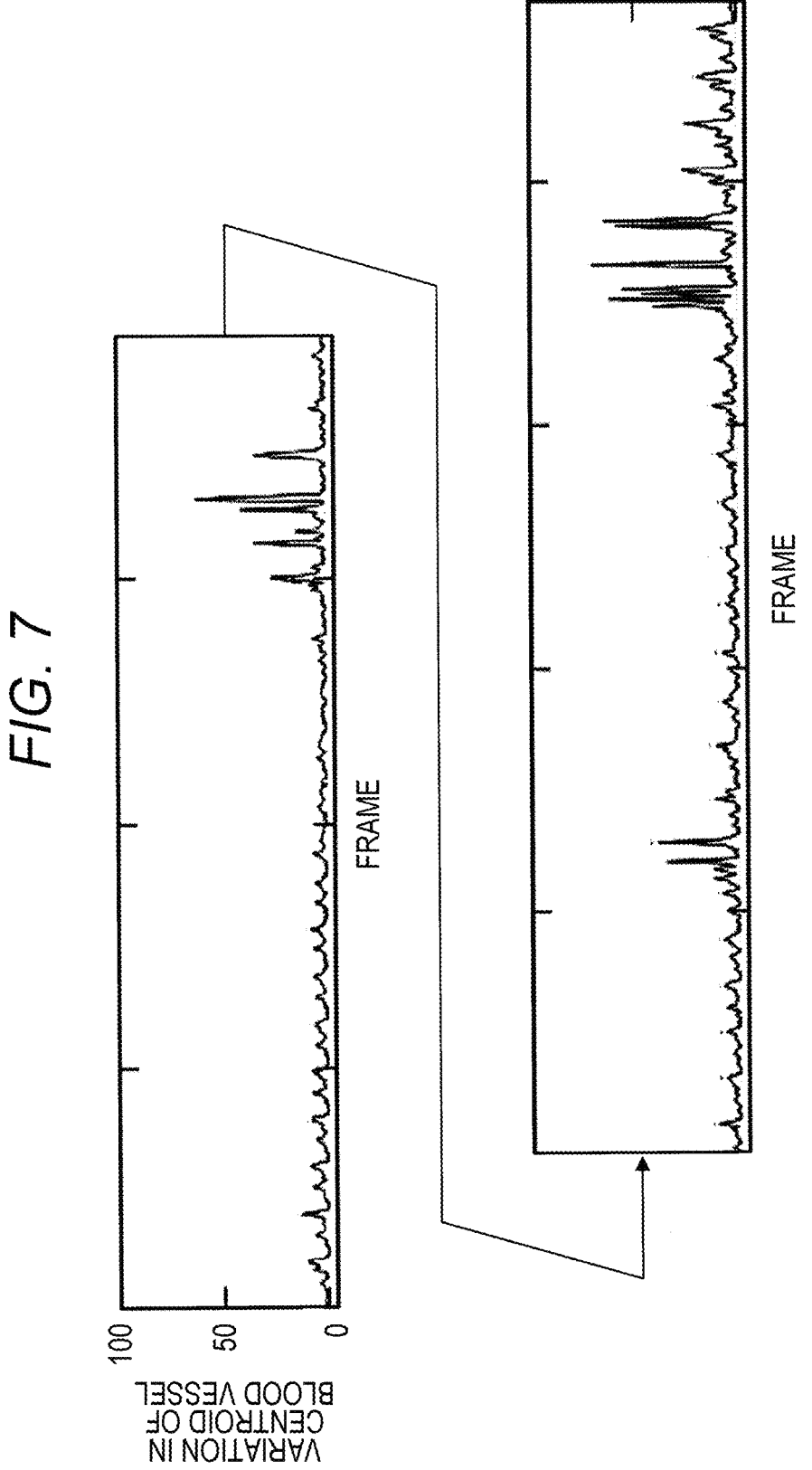
FIG. 7 is a diagram illustrating an example of variations in centroid of a blood vessel.

FIG. 7 is a diagram illustrating an example of variations in the centroid of the blood vessel. In the drawing, the horizontal axis represents frames, and the vertical axis represents variations in the centroid of the blood vessel. A change in the relative positional relationship between the blood vessel and the catheter changes due to the influence of heartbeat causes a change in the shape and position of the blood vessel on the cross-sectional image of the blood vessel. Therefore, variations in the centroid of the blood vessel for each frame appear as a pulsatile flow (i.e., unstable variations) as illustrated in FIG. 7. Note that, in the drawing, there is a frame having a peak of variations in the centroid of the blood vessel larger than the other peaks, but the frame corresponds to a location where a side branch is present, and this is because the centroid position of the blood vessel largely varies in a manner that depends on whether the blood vessel has a side branch.

The frame identification unit 55 detects a peak of variations in the centroid of the blood vessel and identifies a frame having the detected peak as a necessary frame. Specifically, the frame identification unit 55 can detect a local maximum of variations in the centroid of the blood vessel calculated for each frame and identify a frame corresponding to the detected local maximum as a necessary frame. Furthermore, at least one of pre-processing or post-processing for the processing of detecting a local maximum may be executed. The pre-processing includes, for example, processing of removing noise from variations in the centroid of the blood vessel by means of filter processing as pre-noise removal. Furthermore, the post-processing includes, for example, (1) processing of removing noise (for example, a smaller local maximum and the like) so as to make a detected local maximum greater than or equal to a certain value, and (2) processing of removing noise (for example, a smaller local maximum and the like) so as to make an interval between adjacent local maxima greater than or equal to a certain interval. As a result, unnecessary noise can be removed.

Figure 8:
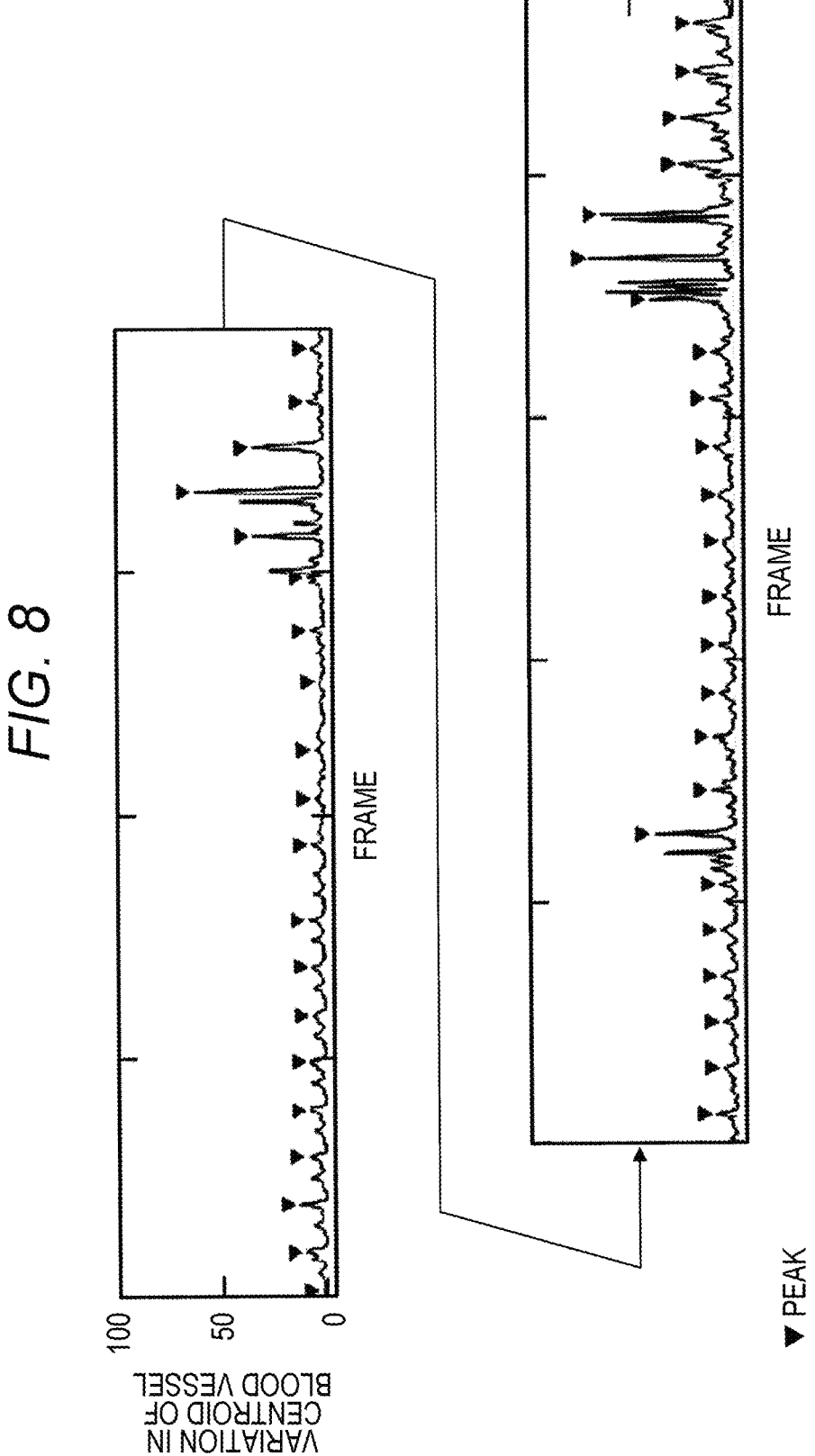
FIG. 8 is a diagram illustrating an example of a method of identifying necessary frames.

FIG. 8 is a diagram illustrating an example of the method of identifying necessary frames. In the drawing, a symbol "▼" indicates a position where the peak of variations in the centroid of the blood vessel is detected, and the corresponding frame becomes a necessary frame. As illustrated in FIG. 8, the necessary frame is identified regardless of a side branch. The necessary frame is a frame having a variation in the centroid of the blood vessel greater than or equal to a predetermined threshold, and is a frame corresponding to the specific heartbeat intervals.

As described above, with the information processing apparatus 50, even in a case where electrocardiogram information or the like cannot be obtained, frames (necessary frames) can be extracted at specific intervals only by acquiring medical image data representing a plurality of frames of cross-sectional images of the blood vessel.

Figure 9:
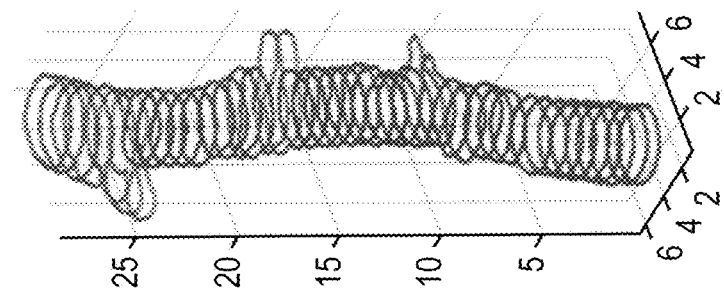
FIG. 9 is a diagram illustrating an example of a result of extracting necessary frames.
Figure 9:
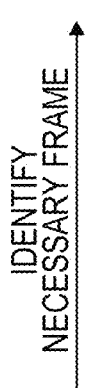
Figure 9:
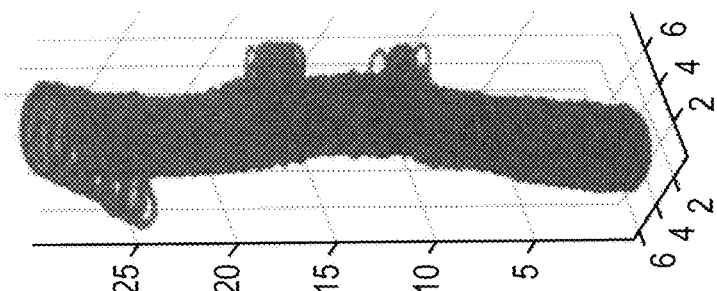

FIG. 9 is a diagram illustrating an example of a result of extracting necessary frames. The figure on the left illustrates the boundaries of the blood vessel of the segmentation data (S1, S2, S3, . . . , Sn) corresponding to the frames 1 to n of the medical image data (G1, G2, G3, . . . , Gn) on a one-to-one basis. In this figure, the boundaries of the blood vessel in all the frames are shown, but the blood vessel boundaries vary between frames due to the influence of heartbeat, which makes the overall blood vessel boundary unclear.

In the figure on the right, only the necessary frames are extracted from all the frames, and the boundaries of the blood vessel of the extracted necessary frames are arranged. When the number of the necessary frames is 1 to n', the frame number n'<the frame number n holds. Note that the original frame 1 and the necessary frame 1 do not necessarily coincide with each other. Similarly, the original frame 2 and the necessary frame 2 do not necessarily coincide with each other. The same applies to the subsequent frames. The frames 1 to n' indicate the indexes of the necessary frames, and do not indicate the indexes of the original frames. In FIG. 9B, the boundaries of the blood vessel in the frames corresponding to the specific heartbeat intervals are shown, which makes the blood vessel boundary in each frame clear.

Next, a method of generating a 3D image of a blood vessel will be described.

Figure 10:
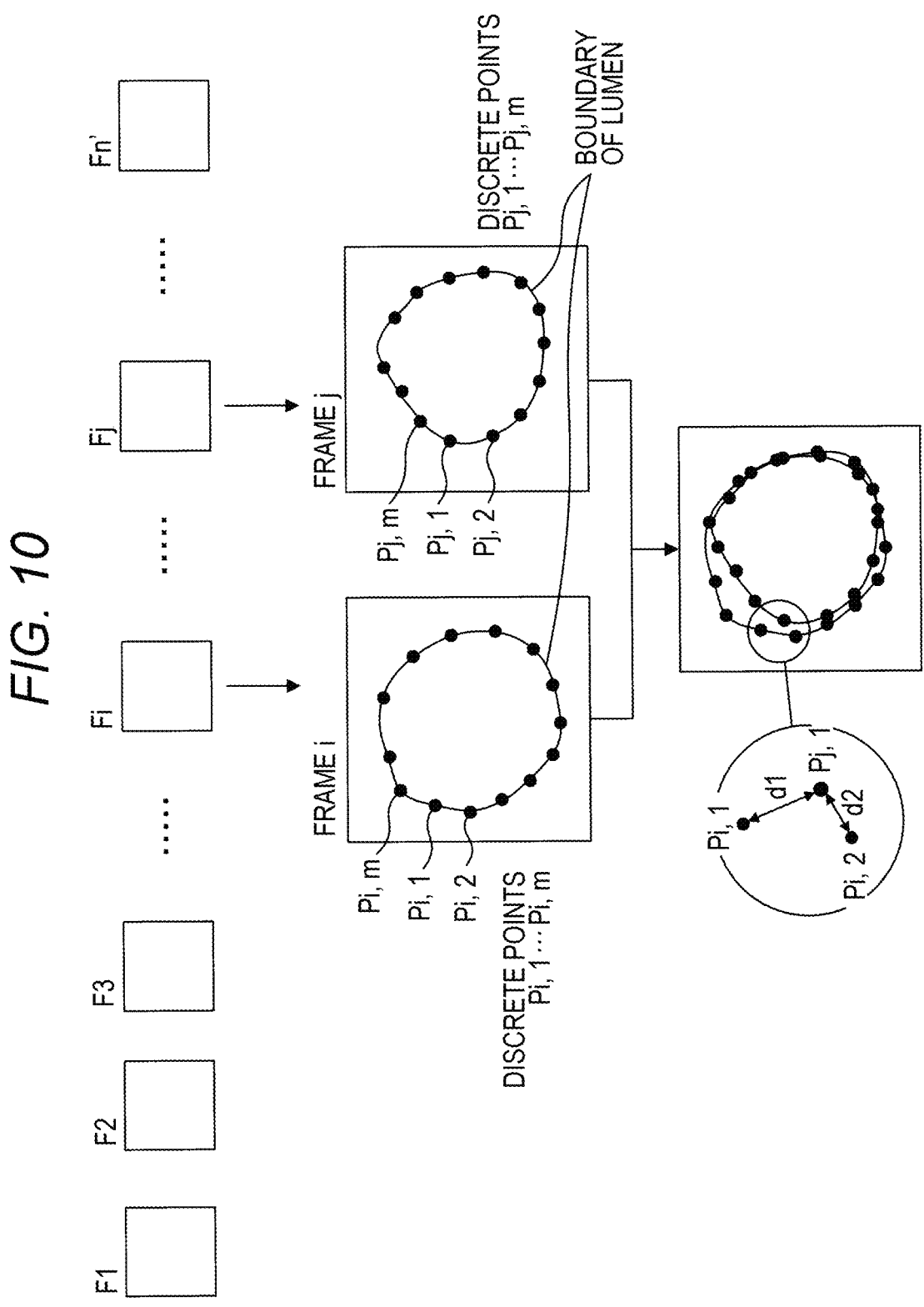
FIG. 10 is a diagram illustrating an example of a method of identifying a corresponding point group of a predetermined site in a case where there is no side branch.

FIG. 10 is a diagram illustrating an example of a method of identifying a corresponding point group of a predetermined site in a case where there is no side branch. Hereinafter, the boundary of the lumen will be described as the predetermined site, but the predetermined site also includes the boundary of the blood vessel. The necessary frames identified by the frame identification unit 55 are denoted as 1, 2, 3, . . . , n'. Segmentation data of the necessary frames are denoted as F1, F2, F3, . . . , Fi, . . . , Fj, . . . , Fn'. The number of frames is n' where n'<the total number of frames n. A frame of interest is denoted as j, and a corresponding frame corresponding to the frame of interest j is denoted as i. The frame of interest j and the corresponding frame i are necessary frames for identifying the corresponding point group. Note that the frame of interest j and the corresponding frame i need not be adjacent frames, and another frame may exist between the frame of interest j and the corresponding frame i.

A discrete point on the boundary of the lumen indicated by the segmentation data Fi of the frame i is represented by P (i, m), and a discrete point on the boundary of the lumen indicated by the segmentation data Fj of the frame j is represented by P (j, m). "m" denotes a number from 1 to m, indicating the number of discrete points. Examples of a method of identifying the discrete points include: (1) a method of sequentially identifying the discrete points at the same angle along the boundary; (2) a method of identifying the discrete points such that the distance between the discrete points is constant; and (3) a method of identifying the discrete points such that the number of the discrete points is constant. As a result, regardless of the shape of the boundary, it is possible to acquire the discrete points in a well-balanced manner while suppressing excessive torsion and the like. Furthermore, the number of discrete points on the boundary of the blood vessel may be less than or equal to the number of discrete points on the boundary of the lumen. As a result, the number of discrete points on the boundary of the blood vessel can be reduced, and the visibility of the mesh of the lumen can be improved.

A distance between the discrete point P (j, 1) of the segmentation data Fj of the frame j and each of the m discrete points P (i, m) (m=1 to m) of the segmentation data Fi of the frame i is calculated, and the discrete point P (i, m) having the shortest distance is identified as a corresponding point. In the example in FIG. 10, when a distance d1 between the discrete point P (j, 1) and the discrete point P (i, 1) and a distance d2 between the discrete point P (j, 1) and the discrete point P (i, 2) are calculated and the calculated distances d1 and d2 are compared, the distance d2 is shorter than the distance d1, and thus the discrete point P (i, 2) is selected. A similar comparison is made for other discrete points.

It is possible to identify, by executing similar processing on each discrete point P (j, m) of the segmentation data Fj of the frame j, the corresponding point group of the boundary of the lumen between the frame i and the frame j.

Figure 11:
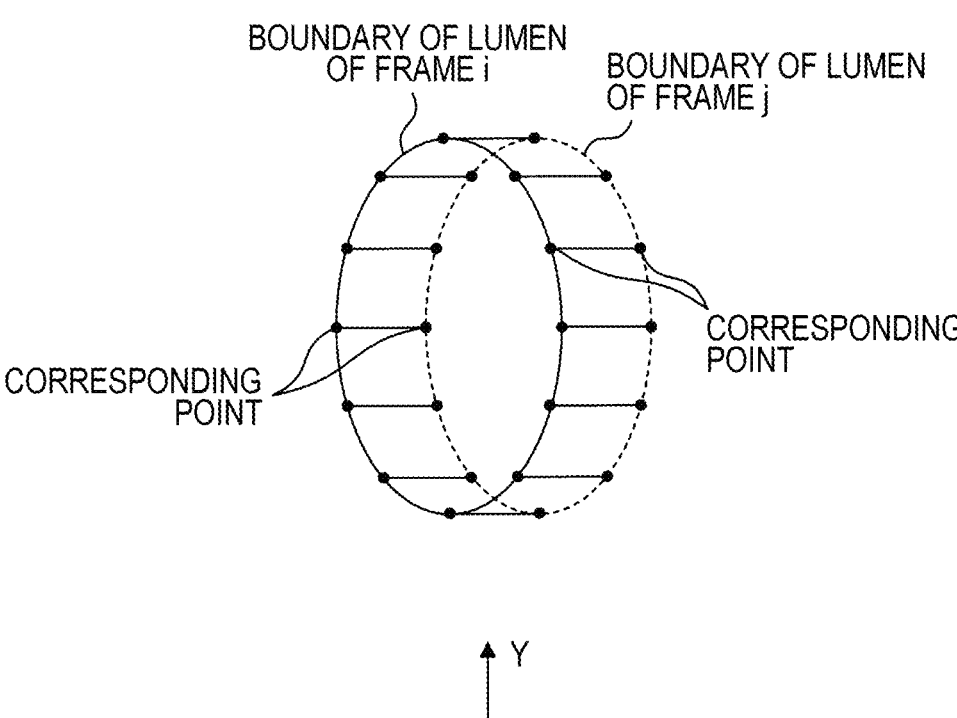
FIG. 11 is a diagram illustrating an example of a method of connecting corresponding point groups.

FIG. 11 is a diagram illustrating an example of a method of connecting corresponding point groups. It is assumed that a discrete point group on the boundary of the lumen indicated by the segmentation data Fi of the frame i and a discrete point group on the boundary of the lumen indicated by the segmentation data Fj of the frame j are associated with each other. The discrete points associated with each other are referred to as corresponding points, and the corresponding points on the boundary are collectively referred to as corresponding point group. The segmentation data Fi of the frame i and the segmentation data Fj of the frame j are separated at an appropriate interval from each other and arranged along the Z-axis direction. The Z axis indicates the long axis direction of the blood vessel. The corresponding points (i.e., the corresponding point group) of the frames i and j are connected by a straight line in the Z-axis direction. Furthermore, corresponding points adjacent on the boundary are connected by a straight line along the boundary. As a result, it is possible to generate a 3D image in which the boundaries of the lumen indicated by the respective pieces of segmentation data of the frames i and j are connected in a mesh shape. Similarly, a 3D mesh image can be generated for the boundary of the blood vessel. It is possible to generate, by executing similar processing on all the frames 1 to n, a 3D mesh image of the blood vessel.

Figure 12:
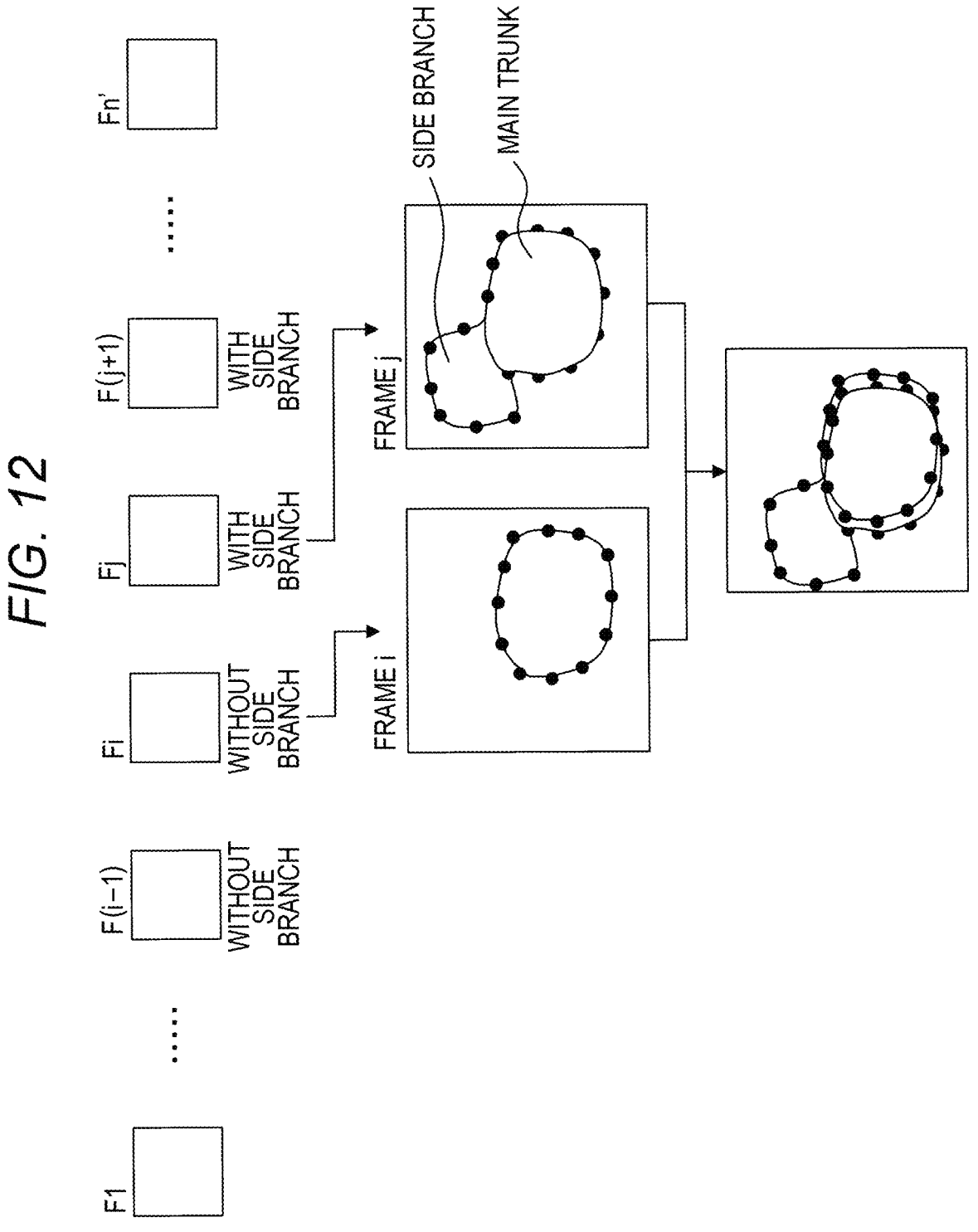
FIG. 12 is a diagram illustrating a first example of a method of identifying a corresponding point group of a predetermined site in a case where there is a side branch.

FIG. 12 is a diagram illustrating a first example of the method of identifying a corresponding point group of a predetermined site in a case where there is a side branch. The presence or absence of the side branch can be determined on the basis of the segmentation data output by the learning model 59. Note that the presence or absence of a side branch can be determined on the basis of the eccentricity of the blood vessel cross-sectional shape. For example, the eccentricity can be obtained by calculating the maximum diameter d1 and the minimum diameter d2 of the lumen diameter on the basis of the boundary of the lumen. The eccentricity can be calculated by an equation of eccentricity=(maximum diameter d1−minimum diameter d2)/maximum diameter d1. The presence or absence of a side branch can be determined according to whether the eccentricity is greater than or equal to a predetermined threshold. Instead of the eccentricity, the circularity may be calculated. The circularity is the ratio of the area of the inner region of the boundary of the blood vessel to the circumferential length of the boundary of the blood vessel. It can be determined that the closer the circularity is to the ratio between the area of the circle and the length of the circumference, the higher the circularity is and the lower the possibility that a side branch is shown. Furthermore, as another determination example of the presence or absence of a side branch, a value obtained by comparing the diameter (e.g., the maximum diameter and minimum diameter) of the target boundary of the blood vessel with the diameter of the boundary of the blood vessel shown in a scanned tomographic image is calculated as a parameter, and the presence or absence of a side branch can be determined according to whether the diameter suddenly changes by a predetermined ratio or more and by a predetermined length or more. As still another determination example, determination may be made using a learning model for determination trained to output accuracy corresponding to the possibility that a side branch is shown in a case where data of the boundary of the lumen and the boundary of the blood vessel is input.

As illustrated in FIG. 12, it is assumed that there is no side branch in the segmentation data F1, . . . , F(i−1), and Fi, and there is a side branch in the segmentation data Fj and F(j+1). In this case, as the corresponding frame, a frame without a side branch and a frame with a side branch can be associated. In the example in FIG. 12, the segmentation data Fi of the frame i is associated with the segmentation data Fj of the frame j. The discrete point group of the boundary of the lumen of the segmentation Fi and the discrete point group of the boundary of the lumen of the main trunk of the segmentation Fj are associated with each other and identified as a corresponding point group, and is subjected to the same processing as the processing illustrated in FIG. 10. On the other hand, the discrete point group of the boundary of the lumen of the side branch of the segmentation Fj is left as is, and is not subjected to the connection processing.

Figure 13:
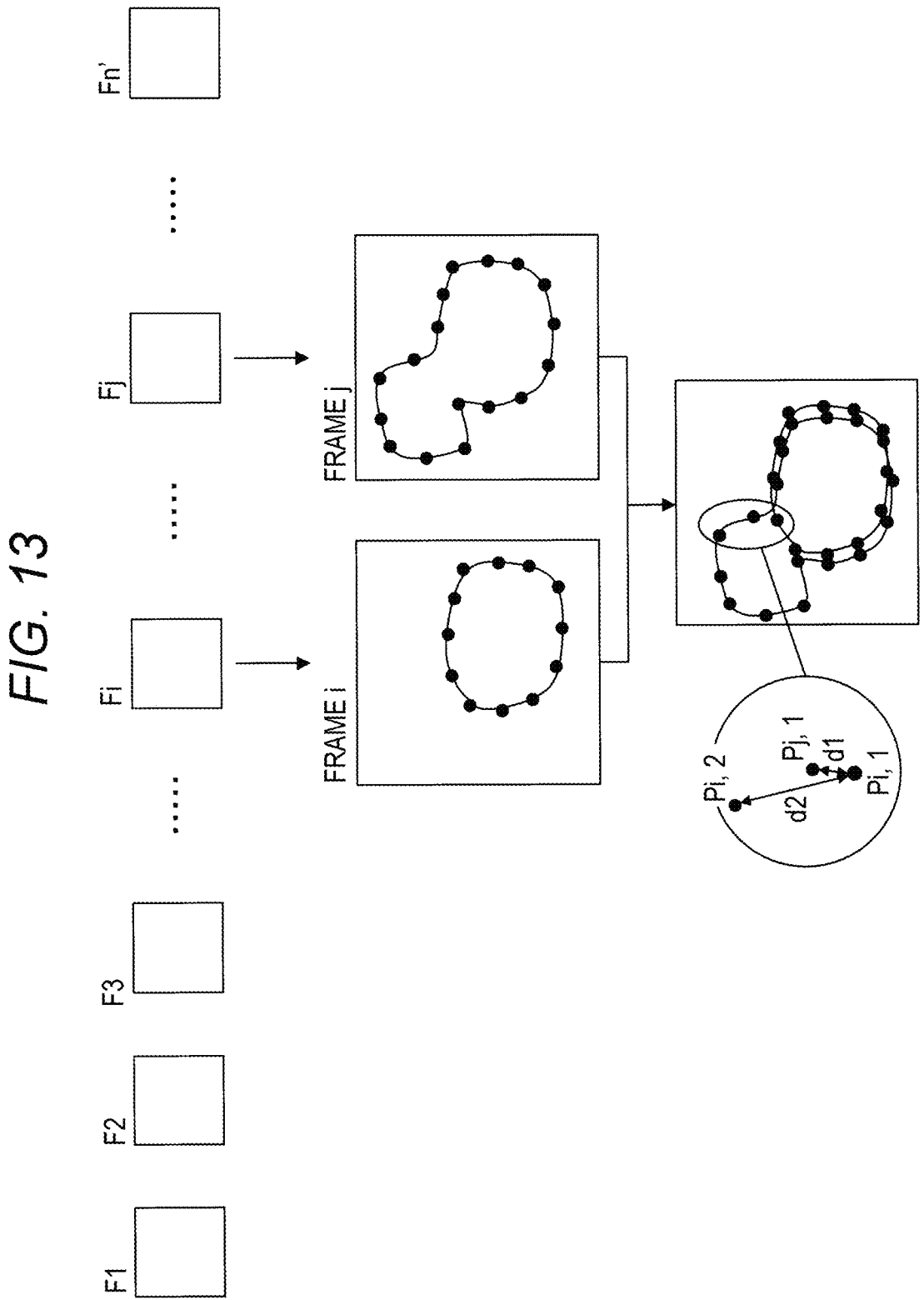
FIG. 13 is a diagram illustrating a second example of the method of identifying a corresponding point group of a predetermined site in a case where there is a side branch.

FIG. 13 is a diagram illustrating a second example of the method of identifying a corresponding point group of a predetermined site in a case where there is a side branch. As illustrated in FIG. 13, a distance d1 between the discrete point P (j, 1) and the discrete point P (i, 1) and a distance d2 between the discrete point P (j, 1) and the discrete point P (i, 2) are calculated. Whether to perform association is determined according to whether the calculated distances d1 and d2 are greater than or equal to a predetermined threshold. For example, since the distance d1 is smaller than the threshold, association is performed. On the other hand, since the distance d2 is longer than the threshold, no association is performed. As described above, when the corresponding points are identified, if the distance between the discrete points is greater than or equal to the threshold, the discrete points are not connected. A similar comparison is made for other discrete points.

As described above, the control unit 51 can identify the corresponding point group of the predetermined site of the blood vessel in two different frames among the necessary frames identified by the frame identification unit 55, and generate the 3D image of the blood vessel on the basis of the identified corresponding point group.

Figure 14A:
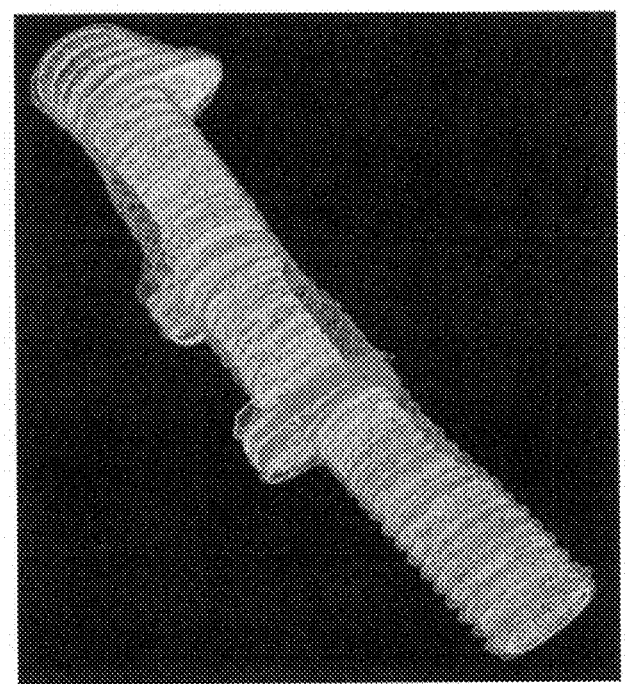
FIG. 14A is a diagram illustrating an example of a simulated 3D image of a blood vessel.
Figure 14B:
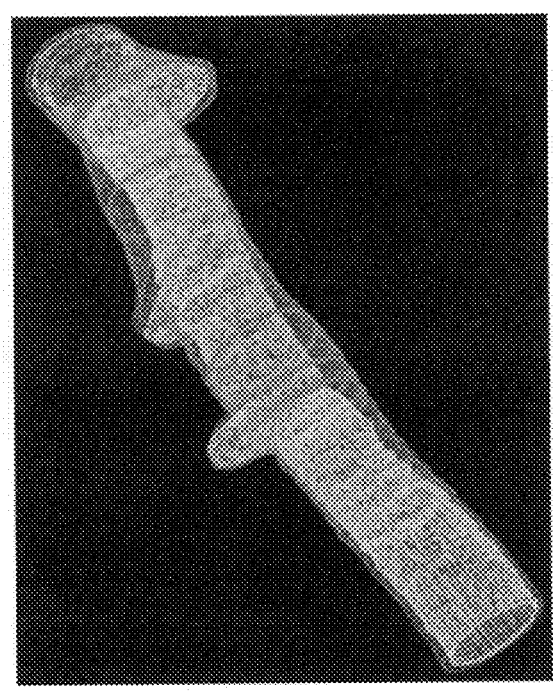
FIG. 14B is a diagram illustrating an example of a simulated 3D image of a blood vessel.

FIGS. 14A and 14B are diagrams illustrating an example of a simulated 3D image of a blood vessel. The 3D image of the blood vessel illustrated in FIGS. 14A and 14B is a 3D image obtained through a simulation of actual processing. FIG. 14A illustrates a 3D image generated through a simulation according to a comparative example. In the comparative example, a 3D image of a blood vessel generated using segmentation data of all frames without identifying a necessary frame is illustrated. In the comparative example, the 3D mesh image becomes quite a bit blurry due to the influence of noise caused by heartbeat.

FIG. 14B illustrates a 3D image generated through a simulation according to the embodiment described above. Since segmentation data using only necessary frames is used, noise caused by heartbeat is removed. As a result, the 3D mesh image is hardly blurry, so that a clear 3D image can be obtained.

Figures 15A, 15B:
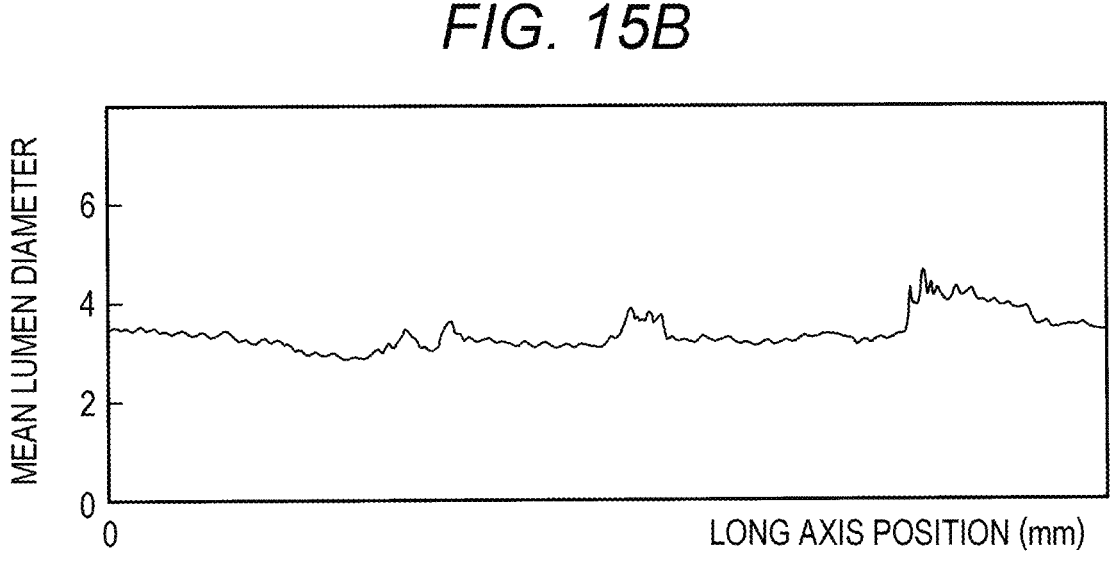
FIG. 15A is a diagram illustrating an example of blood vessel information based on necessary frames.
FIG. 15B is a diagram illustrating an example of the blood vessel information based on necessary frames.

FIGS. 15A and 15B are diagrams illustrating an example of blood vessel information based on necessary frames. In FIG. 15A, the horizontal axis represents the long axis position of the blood vessel, and the vertical axis represents the plaque area ratio (i.e., the plaque burden). The plaque area ratio illustrated in FIG. 15A uses the segmentation data using only necessary frames, so that noise caused by heartbeat is removed, the plaque area ratio can be calculated with high accuracy. That is, the control unit 51 can generate information on plaque distribution (i.e., the plaque burden) in the axial direction of the blood vessel on the basis of the region information on the predetermined site of the blood vessel in each identified necessary frame. It is possible to determine, by obtaining the blood vessel information as illustrated in FIG. 15A, at which position in the blood vessel a stent should be placed, how long the stent should be, and the like, for example.

In FIG. 15B, the horizontal axis represents the long axis position of the blood vessel, and the vertical axis represents the mean lumen diameter. The mean lumen diameter illustrated in FIG. 15B uses the segmentation data using only necessary frames, so that noise caused by heartbeat is removed, the mean lumen diameter can be calculated with high accuracy. That is, the control unit 51 can calculate the mean lumen diameter in the axial direction of the blood vessel on the basis of the region information on the predetermined site of the blood vessel for each identified necessary frame. It is possible to determine, by obtaining the blood vessel information as illustrated in FIG. 15B, a stent diameter, for example.

FIG. 16 is a diagram illustrating an example of a process performed by the information processing apparatus 50. For convenience, the following description will be given on the assumption that the control unit 51 perform the process. First, the control unit 51 acquires medical image data (S11), inputs the acquired medical image data into the learning model 59 to acquire region information on a predetermined site of the blood vessel (for example, the boundary of the blood vessel and the boundary of the lumen) for each frame (S12).

The control unit 51 calculates a feature value (for example, the centroid of the blood vessel) for each frame on the basis of the acquired region information on the predetermined site (S13), and calculates variations in the feature value for each frame on the basis of a difference in the feature value between the frames (S14).

The control unit 51 detects a local maximum (or peak) of the variations calculated for each frame to identify a necessary frame (S15). As for the identification of a necessary frame, refer to FIG. 8, for example. The control unit 51 identifies a corresponding point group of the predetermined site in two different necessary frames among the identified necessary frames (S16), and generates a 3D mesh image of the blood vessel using the identified corresponding point group (S17).

The control unit 51 calculates a plaque area ratio and a mean lumen diameter in the long axis direction of the blood vessel on the basis of the region information on the predetermined site in the identified necessary frames (S18), and ends the process. Note that step S18 can branch off from step S15 and be executed in parallel with steps S16 and S17.

The embodiments described above are illustrative in all respects and are not restrictive. The scope of the present invention is defined by the claims, and includes meanings equivalent to the claims and all modifications within the scope.

What is claimed is:

1. A medical imaging apparatus for generating a three-dimensional image of a vessel, comprising:
   a catheter including a probe and insertable into the vessel, wherein the catheter is configured to generate cross-sectional images of the vessel from signals emitted from the probe and received by the probe; and
   a processor configured to:
      control the catheter to emit the signals and acquire a series of cross-sectional images of the vessel therefrom,
      calculate a series of feature values of the vessel corresponding to the series of cross-sectional images,
      determine local maximums of variations in the series of feature values,
      select two or more of the cross-sectional images corresponding to the local maximums, and
      generate a three-dimensional image of the vessel using the selected images.

2. The medical imaging apparatus according to claim 1, wherein the processor is configured to:
   input the cross-sectional images to a computer model to generate region information indicating one or more of predetermined regions of the vessel included in each of the cross-sectional images, and
   calculate the feature values based on the region information.

3. The medical imaging apparatus according to claim 2, wherein the computer model has been trained to classify each of regions included in an input cross-sectional image of the vessel into one of the predetermined regions.

4. The medical imaging apparatus according to claim 3, wherein the predetermined regions include a first region outside the vessel, a second region including plaque, and a third region including a lumen of the vessel.

5. The medical imaging apparatus according to claim 2, wherein the processor is configured to generate information indicating plaque distribution in an axial direction of the vessel based on the region information for each of the selected images.

6. The medical imaging apparatus according to claim 2, wherein the processor is configured to calculate a mean lumen diameter of the vessel based on the region information for each of the selected images.

7. The medical imaging apparatus according to claim 1, wherein each of the feature values represents a centroid position of the vessel.

8. The medical imaging apparatus according to claim 1, wherein each of the feature values represents a mean lumen diameter of the vessel.

9. The medical imaging apparatus according to claim 1, wherein the processor is configured to:

determine a group of points corresponding to a predetermined region of the vessel in each of the selected images, associate the group of points of each of the selected images with the group of points of another of the selected images, and generate the three-dimensional image of the vessel based on the associated groups of points.

10. The medical imaging apparatus according to claim 1, wherein the processor is configured to determine whether a side branch of the vessel is present using maximum and minimum diameters of the vessel in each of the selected images.

11. A method for generating a three-dimensional image of a vessel, the method comprising:

controlling a catheter including a probe and inserted into the vessel to emit signals and acquiring a series of cross-sectional images of the vessel therefrom;

calculating a series of feature values of the vessel corresponding to the series of cross-sectional images;

determining local maximums of variations in the series of feature values;

selecting two or more of the cross-sectional images corresponding to the local maximums; and generating a three-dimensional image of the vessel using the selected images.

12. The method according to claim 11, further comprising:

inputting the cross-sectional images to a computer model to generate region information indicating one or more of predetermined regions of the vessel included in each of the cross-sectional images, wherein the feature values are calculated based on the region information.

13. The method according to claim 12, wherein the computer model has been trained to classify each of regions included in an input cross-sectional image of the vessel into one of the predetermined regions.

14. The method according to claim 13, wherein the predetermined regions include a first region outside the vessel, a second region including plaque, and a third region including a lumen of the vessel.

15. The method according to claim 12, further comprising:

generating information indicating plaque distribution in an axial direction of the vessel based on the region information for each of the selected images.

16. The method according to claim 12, further comprising:

calculating a mean lumen diameter of the vessel based on the region information for each of the selected images.

17. The method according to claim 11, wherein each of the feature values represents a centroid position of the vessel.

18. The method according to claim 11, wherein each of the feature values represents a mean lumen diameter of the vessel.

19. The method according to claim 11, further comprising:

determining a group of points corresponding to a predetermined region of the vessel in each of the selected images; and associating the group of points of each of the selected images with the group of points of another of the selected images, wherein the three-dimensional image of the vessel is generated based on the associated groups of points.

20. A non-transitory computer readable storage medium storing a program causing a computer to execute a method for generating a three-dimensional image of a vessel, the method comprising:

controlling a catheter including a probe and inserted into the vessel to emit signals and acquiring a series of cross-sectional images of the vessel therefrom;

calculating a series of feature values of the vessel corresponding to the series of cross-sectional images;

determining local maximums of variations in the series of feature values;

selecting two or more of the cross-sectional images corresponding to the local maximums; and generating a three-dimensional image of the vessel using the selected images.

* * * * *